United States Patent [19]

Demopoulos

[11] Patent Number: 4,851,450
[45] Date of Patent: Jul. 25, 1989

[54] COMPOUNDS FOR INHIBITION OF PLATELET ACTIVATING FACTOR ACTIVITY

[76] Inventor: Constantine A. Demopoulos, 39 Anafis Street, Athens, Greece, GR11364

[21] Appl. No.: 113,633

[22] Filed: Oct. 26, 1987

[51] Int. Cl.$^4$ .............................................. A01N 31/00
[52] U.S. Cl. .................................. 514/738; 514/834; 514/929; 514/930; 514/870
[58] Field of Search .................... 424/2, 170, 180, 226, 424/299, 305, 343; 514/738, 739, 870, 762, 822, 834, 929, 930; 436/69; 422/73

[56] References Cited

U.S. PATENT DOCUMENTS 4,507,216 2/1985 Braid et al. ............................. 44/76
4,626,581 12/1986 Weigel ................................... 526/288
4,704,218 11/1987 Horodysky et al. ..................... 44/53

OTHER PUBLICATIONS

Tselepis, et al., Comp. Biochem. Physiol. 87C(1), 41–46 (1987).
Andrikopoulos, et al., Z. Naturforsch. 41c, 396–402 (1986).
Demopoulos, et al., J. Biol. Chem. 254, 9355–9358 (1979).
Bergmeyer et al., "Methods of Enzymatic Analysis", 3, 1196, Academic Press, N.Y. (1974).
Tang et al., Chemistry and Physics of Lipids 17, 169–175 (1976).

Primary Examiner—Barry S. Richman
Assistant Examiner—T. J. Wallen
Attorney, Agent, or Firm—Kilpatrick & Cody

[57] ABSTRACT

The present invention is a group of biologically active agents, di-hydroxy alkyl glycerols with vicinal hydroxyl groups and their acetyl-derivatives having the general formula:

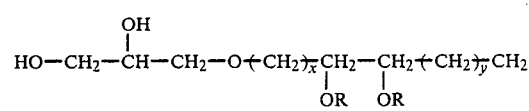

where R is selected from the group of H and $CH_3CO-$ and $x+y$ is between 9 and 21; and methods for their synthesis. The compounds of the present invention are synthesized starting with an unsaturated 1-O-alkyl-glycerol of the formula:

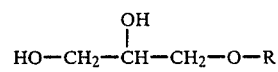

where R is an unsaturated alkyl group with a chain length of 12 to 24 carbon atoms and introducing a vicinal hydroxyl into the alkyl carbon chain using either osmium tetroxide or performic acid, produced by mixing formic acid with hydrogen peroxide.

The new glycerol ether derivatives exert platelet activating factor (PAF)-like action in vitro in low concentrations, and, surprisingly, in higher doses act as selective antagonists of PAF, or 1-O-alkyl-2-O-acetyl-sn-glyceryl-3-phosphorylcholine (AGEPC), activities. These compounds are therefore useful under some conditions in the prevention and/or treatment of the undesirable effects of PAF secretion, including platelet aggregation, serotonin secretion, and decreased systolic blood pressure.

19 Claims, 4 Drawing Sheets

TIME
Washed rabbit platelet aggregation profile induced by the Acetylated Lipids or DAG Washed rabbit platelet aggregation profile induced by the Acetylated Lipids or DAG

COMPOUNDS FOR INHIBITION OF PLATELET ACTIVATING FACTOR ACTIVITY

The present invention is in the area of chemical compounds which have an effect on platelets, specifically platelet activating factors such as 1-O-alkyl-2-acetyl-sn-glyceryl-3-phosphorylcholine.

BACKGROUND OF THE INVENTION

Platelet activation is an early step in many allergic and inflammatory reactions. A key mediator to platelet activation is a glycerol ether lipid containing an acetyl-group. "Platelet-activating factor" (PAF), a natural compound having the structural formula: 1-O-alkyl-2-acetyl-sn-glyceryl-3-phosphorylcholine (AGEPC), as described by Demopoulos et al. in the J. Biol. Chem. 254, 9355–9358 (1979).

PAF is excreted by several types of leukocytes and other cells after immunological and/or certain types of nonimmunological stimulation. The compound activates platelets to aggregate and excrete serotonin, histamine and several granular constituents. In addition, PAF has a wide spectrum of diverse, intravascular, cardiovascular-pulmonary and cutaneous effects, including vasodilation, hypotension, increase in vascular constriction and edema.

Due to the number of effects PAF exerts on the body, some of which are detrimental, such as asthma, it is desirable to have inhibitors of PAF activity and secretion. Unfortunately, to date, there have been no compounds which act in a specific manner to either inhibit secretion or the action of PAF on leukocytes or platelets.

It is therefore an object of the present invention to provide compounds which specifically inhibit PAF activity.

It is another object of the present invention to provide dihydroxy alkyl glycerols with vicinal hydroxyl groups and their acetyl derivatives having biological activity, and methods for their synthesis.

SUMMARY OF THE INVENTION

The present invention is a group of biologically active agents, di-hydroxy alkyl glycerols with vicinal hydroxyl groups

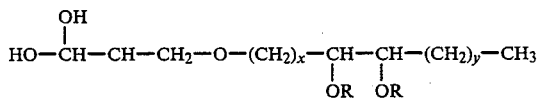

and x+y is between 9 and 21; and methods for their synthesis. The compounds of the present invention are synthesized starting with an unsaturated 1-O-alkyl-glycerol of the formula:

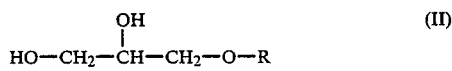

where R is an unsaturated alkyl group with a chain length of 12 to 24 carbon atoms.

The vicinal hydroxyl can be introduced into the alkyl carbon chain of the above compound using (a) Osmium tetroxide or (b) performic acid, produced by mixing formic acid with hydrogen peroxide.

Despite the differences in structures, the new glycerol ether derivatives exert PAF-like action in vivo and in vitro, causing platelet aggregation with the same pattern as PAF in studies using washed rabbit platelets and dose-dependent secretion of serotonin with a non-cytolytic mechanism. Further, surprisingly, in higher doses, the compounds are selective antagonists of PAF activity.

DETAILED DESCRIPTION OF THE INVENTION

Figure 1:
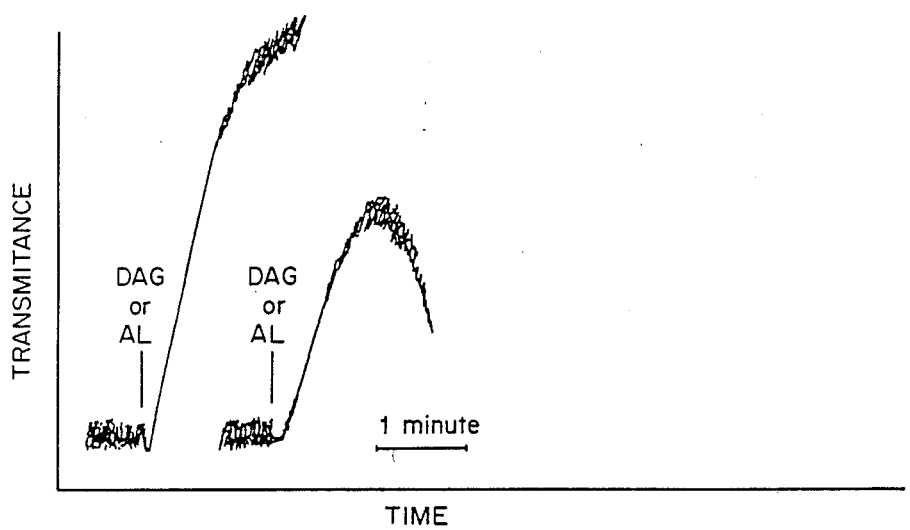
FIG. 1 is a graph of the effect of 9,10 dihydroxyoctadecyl-glycerol (compound III or DAG) and acetylated lipids: acetylated 9,10 dihydroxy-octadecyl glycerol (compound IV or ADAG), acetylated sphingosine sulfate (AS), acetylated cerebrosides (ACer), acetylated gangliosides (AGan), and acetylated sphingomyelin (ASM), on platelet aggregation (transmittance versus time).

The present invention, compounds which have PAF-like activity at low concentrations and (a) The unsatyrated 1-O-alkyl-glycerol selective antagonists to PAF activity at higher concentrations, di-hydroxy alkyl glycerols with vicinal hydroxy groups, and their acetyl derivatives, are synthesized by either of two methods, as follows:

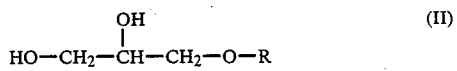

in dry ether is treated with osmium tetroxide in the presence of pyridine with stirring for 48 hrs at 10° C. The reaction is stopped by the addition of mannitol in 10% aqueous potassium hydroxide with vigorous shaking.

The solution separates to form an oily layer containing the desired compounds. The remaining solution is then extracted with chloroform-methanol and the chloroform layer is mixed with the oily product. The synthesized compound is purified by preparative TLC.

(b) The unsaturated 1-O-alkyl-glycerol (II) is mixed with formic acid. 30% $H_2O_2$ is added dropwise, with stirring, at a temperature not above 20° C. After stirring for 1 h, the formic acid is removed under reduced pressure and the oily residue is refluxed with methanolic hydrochloric acid for 1 h at 75° C. The reaction mixture is distilled under reduced pressure.

The synthesized compound is purified by preparative thin layer chromatography (TLC) using chloroform-methanol-water (90:10:1) as the developing solvent system. The synthesized compound has Rf: 0.4.

The acetylated derivatives of the above compounds may be prepared either by (a) treatment with acetic anhydride for 2 h at 60° C. in a small volume of chloroform or (b) treatment with acetylchloride in the presence of pyridine.

The acetylated product is purified by preparative TLC with the following developing solvent systems: initial separation in chloroform:methanol:water (90:10:1); followed by rechromatography of the area with Rf 0.9 in petroleum ether:diethyl ether:acetic acid (85:15:1). The purified acetylated compound has Rf 0.05.

The following non-limiting examples are provided to more clearly illustrate the methods and compounds of the present invention.

Example One: Preparation of 9,10-Dihydroxy-Octadecyl Glycerol (Compound III).

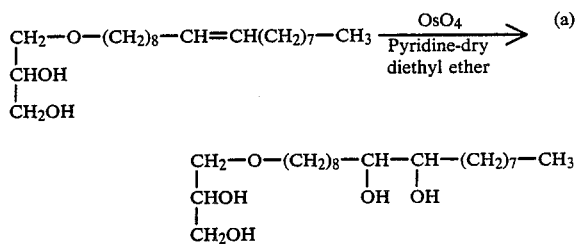

Selachyl alcohol (0.25 g), Osmium tetroxide (0.2 g) and pyridine (0.11 ml) were added in 5 ml dry ether, under anhydrous conditions. The solution was cooled to a temperature not above 10° C., then stirred for 48 hrs. 100 ml Mannitol (2 g) in 10% aqueous potassium hydroxide was added and the mixture well shaken. The oily organic layer was collected and the aqueous solution was extracted several times with a chloroform-methanol (2:1) solution. All extracts were combined, dried with $Na_2SO_4$ are condensed into 2–3 ml volume for purification by TLC.

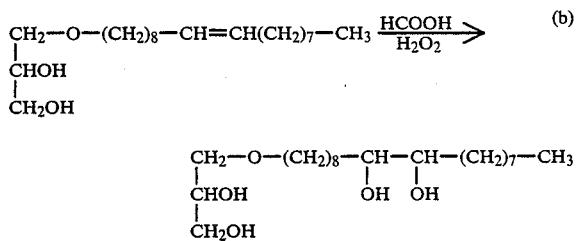

1.0 g (2.9 mmoles) of selachyl alcohol was placed in a round 10 ml flask. 2.0 ml of 87% formic acid were added. The flask was placed in a water bath to maintain the temperature at less than 20° C. The yellowish solution separated into two layers, acid and alcohol. About 1.0 ml of 30% hydrogen peroxide was added dropwise with stirring over 15 min, until the solution became transparent. Stirring was continued for about 1 h. Next, formic acid was distilled under reduced pressure and 2 ml of methanolic hydrochloric acid (hydrochloric acid:methanol 1:5) were added to the oily residue. The mixture was refluxed at 75° C. for 1 h (water bath), cooled and the organic solvent removed by distillation under reduced pressure. A white oily residue remained.

Example Two: Purification of 9,10-Dihydroxy-Octadecyl Glycerol Compound (III).

The white oily residue was dried down, redissolved in a small volume of chloroform-methanol (1:1) and applied to a preparative TLC plate coated with silica gel G 0.5 mm thickness. A mixture of chloroform:methanol:water (90:10:1) (v/v/v) was used as the developing system. The silica area having Rf:0.4 containing the synthesized compound was scraped off and extracted with chloroform-methanol (1:1).

Example Three: Preparation of Tetra-Acetyl-9,10-Dihydroxy-Octadecyl Glycerol (Acetylated derivative of 9,10-Dihydroxy-Octadecyl Glycerol) (Compound IV).

0.2 g of the 9,10-dihydroxy-octadecyl glycerol (III) was dissolved in a small volume of chloroform (0.5 ml) in a screw tube and 2 ml acetic anhydride added. The reaction mixture was placed in a water bath for 2 h at 60° C., then dried down under a nitrogen stream. The residue was redissolved in chloroform:methanol:water (1:2:0.8) (v/v/v) and separated into phases by the addition of the appropriate amounts of chloroform and water to a final ratio of 1:1:0.9 (v/v/v). The synthesized compound (IV) is partioned in the chloroform phase.

Example Four: Purification of Tetra-Acetyl-9,10-Dihydroxy-Octadecyl Glycerol (Compound IV).

The chloroform phase obtained in Example 3 was dried down, redissolved in a small volume of chloroform-methanol (1:1) and applied to a preparative TLC plate coated with silica gel G 0.5 mm in thickness. The plate was developed in a mixture of chloroform:methanol:water (90:10:1) (v/v/v) as the solvent system. The silica area having a Rf of 0.9 was scraped off and extracted with chloroform:methanol (1:1) (v/v). This extract was re-chromatographed using petroleum ether-diethyl ether-acetic acid (85:15:1) (v/v/v) as the developing system. The area with an Rf of 0.05 was scraped off and extracted as above.

Example Five: Effects of 9,10-dihydroxy-octadecyl glycerol and its tetra acetyl-derivative on Platelet Aggregation and Serotonin Secretion.

FIG. 1 is a graph of the effect of 9,10 dihydroxy-octadecyl glycerol (compound III or DAG) and acetylated lipids: acetylated 9,10 dihydroxy-octadecyl glycerol (compound IV or ADAG), acetylated sphingosine sulfate (AS), acetylated cerebrosides (ACer), acetylated gangliosides (AGan), and acetylated sphingomyelin (ASM), on platelet aggregation.

As determined by the procedure of Demopoulos et al., J. Biol. Chem. 254, 9355–9358 (1979), the teachings of which are incorporated herein, the 9,10-dihydroxy-octadecyl glycerol (compound III) and its tetra acetyl-derivative (compound IV) induce a monophasic irreversible aggregation of washed rabbit platelets and a reversible aggregation at lower concentrations with a profile similar to the profile generated by AGEPC. The aggregations are also non-cytotoxic, $Ca^{2+}$ dependent and not affected by indomethacin (10 μM) and CP/CPK (0.7 mM/13 u/ml).

The procedure is as follows: PAF and the various test lipid compounds are assessed for platelet stimulatory activity as briefly described. Rabbit platelets, internally labeled with [$^3$H]serotonin (New England Nuclear; 28.2 Ci/mmol) are washed on Ficoll-Paque cushions and adjusted to $2.5 \times 10^8$ platelets/ml of Tyrode's buffer, pH 7.2. Appropriate dilutions of PAF or the test lipids are prepared in pyrogen-free 0.15M NaCl containing 2.5 mg/ml of crystallized bovine serum albumin; the albumin is required for dispersion of PAF and the test lipids. Four microliters of the various dilutions of PAF and test lipids are added to 200 μl of prewarmed (37° C.) [$^3$H]serotonin-labeled platelets in plastic test tubes and the reaction mixture was incubated for 60 s at which time 20 μl of cold 1.5 m formaldehyde were added to stop the reactions. The tubes were immediately cooled to 0° C., centrifuged at 2200×g for 10 min and the supernatants were assayed for percentage of [$^3$H]serotonin secretion relative to 100% controls prepared by the addition of Triton X-100 to 200 μl of the starting platelet suspension. The data were plotted linearly and 1 unit of activity was defined as the amount of PAF or test lipids required to effect 50% serotonin release.

Cross-desensitization studies of platelets were also performed as described by Demopoules et al: [$^3$H]Serotonin-labeled platelets are prepared and resuspended in Tyrode's buffer, pH 7.2, containing 100 μM EGTA (ethylene glycol bis(β-aminoethyl ether) N,N,N',N'-tetraacetic acid) and no calcium. The platelets are then divided into portions to which is added either 10 units/ml of PAF, the test lipid, or albumin-saline as a control. Following incubation at 37° C. for 20 min, the platelets were washed twice prior to resuspension in Tyrode's buffer, pH 7.2, containing $1.3 \times 10^{-3}$M calcium. The desensitized and control platelets are then tested for their respective reactivity to the test compound or thrombin (purified α-thrombin, 0.25 units/ml).

Figure 2A:
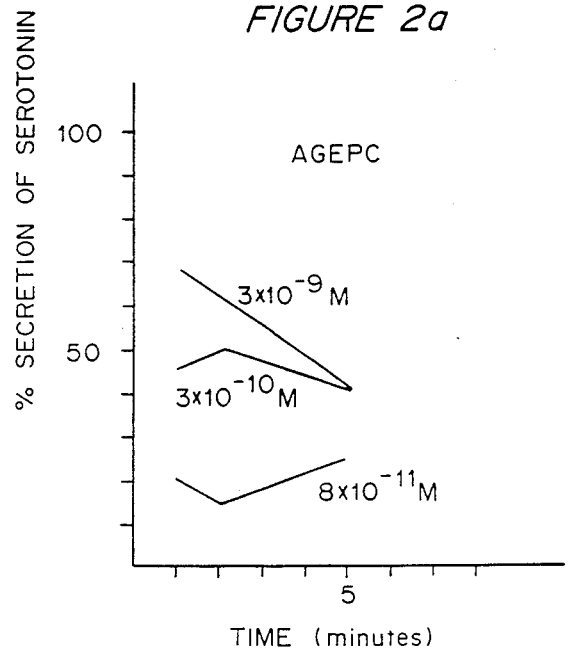
FIG. 2a, b, and c are the results of kinetic studies of serotonin secretion (%secretion vs. time in min) at 1 and 5 min after the addition of AGEPC (FIG. 2a); ACer (FIG. 2b), showing dose dependent secretion; and ADAG, DAG, and AGan (FIG. 2c), showing results comparable to those of AGEPC.
Figure 2B:
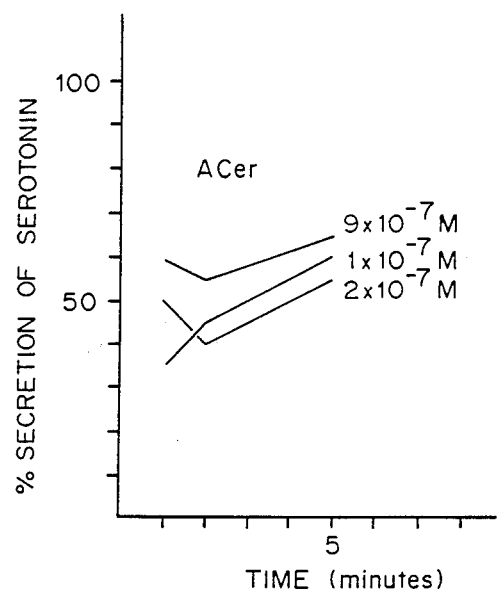
Figure 2C:
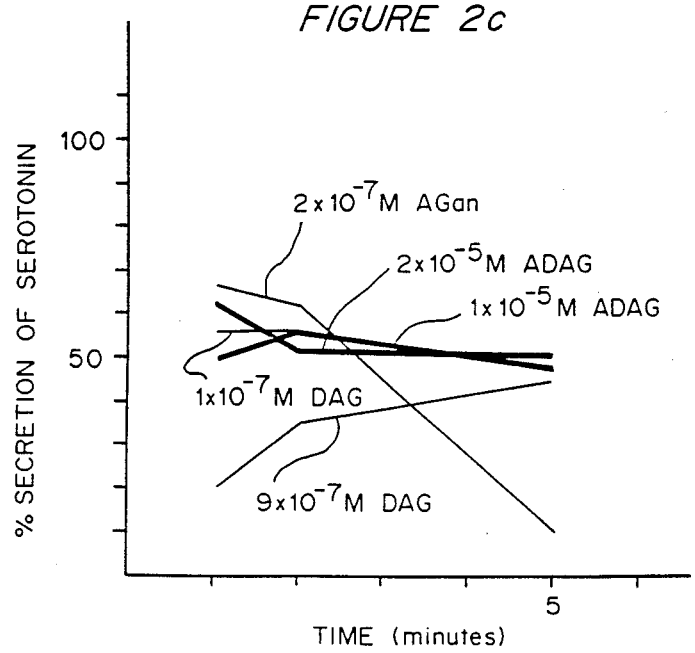

FIG. 2 shows the results of kinetic studies of serotonin secretion at 1 and 5 min after the addition of AGEPC (FIG. 2a); ACer (FIG. 2b), demonstrating dose dependent secretion; and ADAG, DAG, and AGan (FIG. 2c), showing aggregation comparable to the aggregation caused by AGEPC. As further described in the table below, the EC$_{50}$ and 50% secretion of $^3$H-serotonin at 2 min are $2 \times 10^{-7}$M and $2 \times 10^{-6}$M, respectively, for the non-acetylated compound III and $2 \times 10^{-6}$M and $9 \times 10^{-6}$M, respectively, for the acetylated compound IV (final concentrations).

Table: Effect of Lipids on Serotonin Secretion by Platelets.

TABLE

| | Effect of Lipids on Serotonin Secretion by Platelets. | | |
|---|---|---|---|
| Lipid | EC$_{50}$ | IC$_{50}$* (final molar concentration) | 50% secr. |
| ADAG | $2 \times 10^{-6}$ | $2.8 \times 10^{-5}$ | $9 \times 10^{-6}$ |
| DAG | $2 \times 10^{-7}$ | $1.6 \times 10^{-5}$ | $2 \times 10^{-6}$ |
| ACer | $5 \times 10^{-7}$ | $5 \times 10^{-5}$ | $8 \times 10^{-7}$ |
| AGan | $6 \times 10^{-8}$ | $8 \times 10^{-7}$ | $10^{-7}$ |
| ASM | $8 \times 10^{-8}$ | $5 \times 10^{-6}$ | $10^{-7}$ |
| AS | $4 \times 10^{-8}$ | $5 \times 10^{-7}$ | $10^{-7}$ |

*for $2 \times 10^{-10}$M AGEPC
Abbreviations: ADAG acetylated 9,10 dihydroxy-octadecyl glycerol; DAG 9,10-dihydroxy-octadecyl glycerol; ACer acetylated cerebrosides; AGan acetylated gangliosides; ASM acetylated sphingomvelin; AS acetylated sphinosine sulfate.

Desensitization and cross desensitization studies were performed with washed rabbit platelets using the method of Demopoules, et al. From the aggregation curves and the $^3$H-serotonin secretions, it appears that the above synthesized compounds III and IV interact with the same receptor sites as PAF but not with the receptor sites of other aggregating agents such as thrombin or ADP.

Example 6: Effect of 9,10 dihydroxy-octadecyl-glycerol on Tetrahymena pyriformis.

Figure 3:
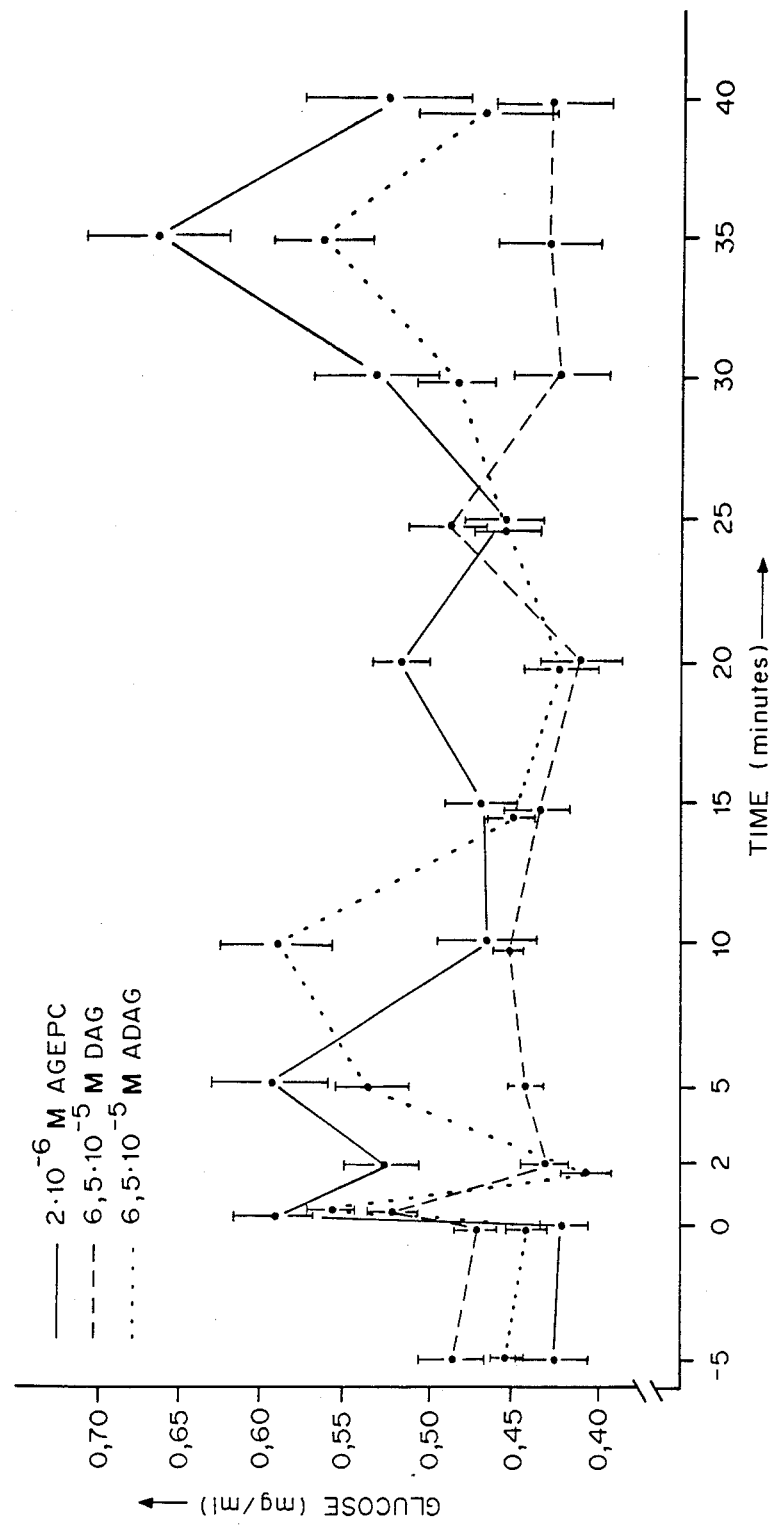
FIG. 3 compares the effect of DAG, ADAG, and AGEPC on glycogenolysis in intact Tetrahymena pyriformis cells (glucose in mg/ml versus time in min).

The above synthesized compounds III and IV have a dramatic influence on glycogenolysis in intact Tetrahymena pyriformis cells, as does PAF. The effects are shown in FIG. 3, comparing the effect of DAG, ADAG, and AGEPC on glycogenolysis in intact Tetrahymena pyriformis cells.

The results were obtained using the following procedure: Tetrahymena pyriformis cells, in log phase, are spun down, washed with saline and resuspended in Tyrodes solution. After 30 min of incubation, the compounds III and IV in bovine serum albumin solution are added and aliquots taken at different time intervals. The aliquots are treated for 2 min in boiled water, sonicated and glucose measured by the method of Bergmeyer et al. (Methods of Enzymatic Analysis, 3, 1196 (Academic Press, N.Y. 1974), the teachings of which are incorporated herein.

Example Seven: Inhibition of PAF Activity by 9,10-dihydroxy-octadecyl glycerol and its tetra acetyl-derivative.

Figure 4:
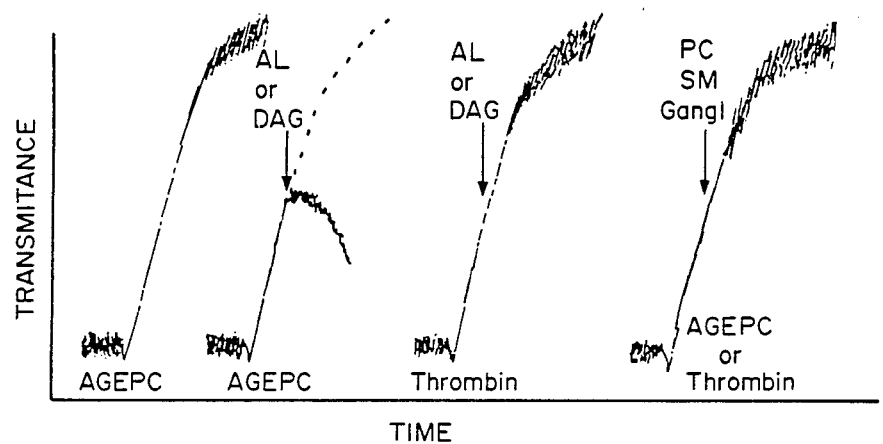
FIG. 4 demonstrates the specific disaggregation of platelets by acetylated lipids (AL) and DAG when added during AGEPC-induced aggregation compared with the addition of thrombin which has no effect on platelet aggregation (transmittance versus time).

FIG. 4 demonstrates the specific disaggregation of platelets by acetylated lipids (AL) and DAG when added during AGEPC-induced aggregation, as compared with the addition of thrombin.

The addition of synthesized compounds III and IV during PAF aggregation of washed rabbit platelets actually interrupts aggregation and causes disaggregation, as demonstrated in FIG. 4, an activity which is therefore quite different from other aggregating agents such as thrombin. Compounds III and IV have an IC$_{50}$ for $2 \times 10^{-10}$M PAF of $1.6 \times 10^{-5}$M and $2.8 \times 10^{-5}$M, respectively, final concentrations.

Example eight: Effect of 9,10-dihydroxy-octadecyl glycerol and its tetra acetyl-derivative on the physiology of rats.

Unlike PAF, compounds III and IV do not cause a fall in the systolic blood pressure (SBP) in rats, as measured using the procedure of Tselepis, et al., Comp. Biochem. Physiol. 87C(1),41–46 (1987), the teachings of which are incorporated herein.

Figure 5:
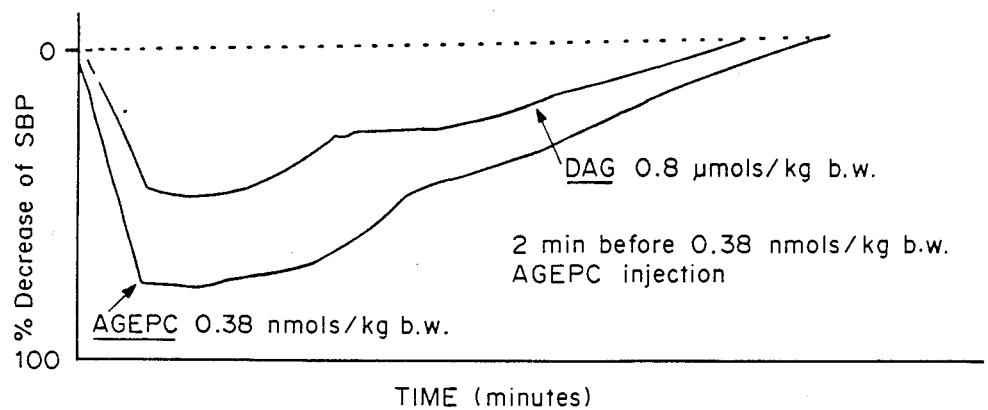
FIG. 5 is a graph of the % decrease in systolic blood pressure in rats as a function of time in minutes after injection of AGEPC, alone or preceded by injection of DAG.

More importantly, however, compound III (0.8 μmols/kg b.w.) inhibits the fall of SBP induced by PAF (0.38 nmols/kg b.w.) in rats if injected (0.8 μmols/kg b.w.) 2 min before PAF and aids in recovery to normal values. FIG. 5 demonstrates these effects for DAG (compound III).

Modifications and variations of the present invention, compounds having biological activity similar to PAF which can also inhibit PAF activity, and methods for their synthesis, will be apparent to those skilled in the art from the foregoing detailed description. Such modifications and variations are intended to come within the scope of the appended claims.

I claim:

1. A method for the preparation of dihydroxy-alkyl alcohols containing acetylated vicinal hydroxylated hydroxyl groups, of the formula:

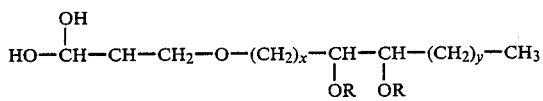

wherein R is selected from the group consisting of H and $CH_3CO$ and x+y is between 9 and 21, comprising hydroxylating an unsaturated 1-O-alkyl-glycerol having a chain length of between 12 and 24 carbon atoms to yield a vicinal hydroxyl group.

2. The method of claim 1 wherein the unsaturated 1-O-alkyl-glycerol is reacted in dry ether with osmium tetroxide in the presence of pyridine.

3. The method of claim 2 wherein the reaction is stopped by the addition of mannitol in potassium hydroxide.

4. The method of claim 1 wherein the 1-O-alkyl-glycerol is mixed with formic acid and $H_2O_2$.

5. The method of claim 4 wherein the formic acid is removed and the reaction product refluxed with methanolic hydrochloric acid.

6. The method of claim 1 wherein the reaction product is acetylated.

7. The method of claim 6 wherein the acetylated reaction product is purified by thin layer chromatography.

8. The method of claim 1 wherein the reaction product is purified by thin layer chromatography.

9. A biologically active composition comprising a compound of a pharmaceutically acceptable carrier and

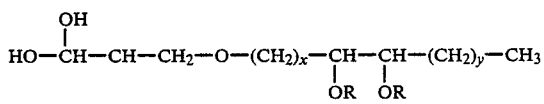

wherein R is selected from the group consisting of H and $CH_3CO$
and x+y is between 9 and 21.

10. The composition of claim 9 wherein R is H and said compound induces platelet aggregation at solution concentrations of approximately $2 \times 10^{-7}M$ or less.

11. The composition of claim 9 wherein R is $CH_3CO$ and wherein said compound induces platelet aggregation at solution concentrations of approximately $2 \times 10^{-6}M$ or less.

12. The composition of claim 9 wherein said compound is in an amount effective to inhibit 1-O-alkyl-2-O-acetyl-sn-glycerol-3-phosphorylcholine activity.

13. The composition of claim 12 wherein R is H.

14. The composition of claim 12 wherein R is $CH_3CO$.

15. The composition of claim 9 wherein R is H and said compound is in an amount which effectively inhibits the decrease in systolic blood pressure induced by 1-O-alkyl-2-O-acetyl-sn-glyceryl-3-phosphorylcholine.

16. A method for inhibiting 1-O-alkyl-2-O-acetyl-sn-glyceryl-3-phosphorylcholine activity comprising providing a biologically active compound of the formula

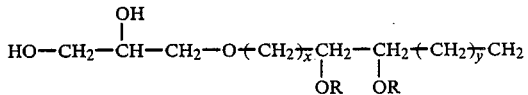

wherein R is selected from the group consisting of H and $CH_3CO$ and x+y is between 9 and 21 in a form and amount effective to inhibit 1-O-alkyl-2-O-acetyl-sn-glyceryl-3-phosphorylcholine activity on intact cells in a solution.

17. The method of claim 16 wherein the solution is blood and said compound is provided in amount and form effective to produce a blood concentration in excess of approximately $1 \times 10^{-5}M$.

18. A method for inducing platelet aggregation comprising providing a biologically active compound of the formula

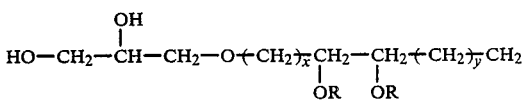

wherein R is selected from the group consisting of H and $CH_3CO$ and x+y is between 9 and 21 in a form and dosage effective to inhibit platelet aggregation in a solution by 1-O-alkyl-2-O-acetyl-sn-glyceryl-3-phosphorylcholine.

19. The method of claim 18 wherein the solution is blood and the compound is in a dosage producing a blood concentration of less than approximately $2 \times 10^{-6}M$ based on estimated blood volume.

* * * * *